United States Patent [19]

Resch

[11] Patent Number: Plant 5,541

[45] Date of Patent: Aug. 20, 1985

[54] VARIEGATED SCHEFFLERA PLANT 'JOSEF RESCH'

[76] Inventor: Josef Resch, 5699 State Rd. 775, Venice, Fla. 33595

[21] Appl. No.: 456,980

[22] Filed: Jan. 10, 1983

[51] Int. Cl.[3] ..... A01H 5/00

[52] U.S. Cl. ..... Plt./88

[58] Field of Search ..... Plt./88

[56] References Cited

U.S. PATENT DOCUMENTS

P.P. 4,187 1/1978 Mastaler ..... Plt./88

*Primary Examiner*—James R. Feyrer

*Attorney, Agent, or Firm*—Hauke and Patalidis

[57] ABSTRACT

A new and distinct variety of *Brassaia actinophylla*, more commonly known as Schefflera, characterized by the extensive and attractive variegation of the foliage.

1 Drawing Figure

FIELD OF THE INVENTION

This invention relates to Schefflera plants in general, and more particularly to a variety which is a variegated Schefflera plant of the species *Brassaia actinophylla.*

BACKGROUND OF THE INVENTION

Schefflera plants are shrubs or trees with few lateral branches, which are very popular as house plants. Their popularity results from their attractive shiny green foliage and their rapid and vigorous growth and hardy habits. The long-stemmed leaves have six to eight glossy leaflets, each about six to eight inches in length, spreading out like an umbrella.

DETAILED DESCRIPTION OF THE PREFERRED EMBODIMENT

The instant variety of variegated Schefflera was discovered growing in a Schefflera seed bed in my nursery in Venice, Fla., and was strikingly outstanding since its variegation made it stand out from other Schefflera growing in the same seed bed.

The accompanying drawings, which illustrate a typical specimen of my new variety of variegated Schefflera plant, disclose the dense arrangement of the foliage, the close noded positions of the leaves, substantially closer noded than conventional Schefflera, having an average of eleven nodes to six inches of trunk. The internode distance varies from about 8–9 mm to about 38–40 mm. The leaves, or leaflets, number from eight to twelve per leaf stem. The size of the leaves is in the range of 18 to 30 cm in length and 7 to 14 cm in width. The thickness of the leaves is in the order of 0.5–0.6 mm. The stem diameter is in the order of 6 mm.

An outstanding characteristic of my new Schefflera is the wide difference in variegation of particular leaves. Some of the leaves on a leaf stem are entirely chartreuse or mimosa in color and entirely devoid of green coloration, while other leaves are chartreuse or mimosa mottled with green variegation along or proximate the edge. Other leaves are chartreuse or mimosa in color generally from an edge of the leaf to the rib, while the area from the rib to the other edge is characterized by dark and light green coloration extending, on some leaves, from the rib to the other edge and on some other leaves from the rib to a serrated line intermediate between the rib and the edge. A few leaves are equally divided in color, one half being cream-mimosa and the other entirely green. The display of color, which gives to some of the leaves a marble-like appearance, extends from generally chartreuse, cream and mimosa colors to principally two different shades of green. The chartreuse-cream coloration is characteristic of new growth leaves, while the cream-mimosa coloration is characteristic of older growth. The variegation extends to the stems and to the top and intermediate portions of the trunk.

Continued airlayer propagation of my new variety of Schefflera has produced plants 3 to 4.5 meters in height, with a spread of 1.2 to 1.8 meters with particular dense foliage towards the top of the trunk, which are very hardy and grow very vigorously. A characteristic of my new variety of Schefflera plant is the vigorous growth, unusual for a variegated plant, 60 cm to 100 cm per year, as compared to a growth of 90 cm to 120 cm per year for non-variegated Schefflera plants. The mature leaves show a strong tenacity to the trunk which remains constant with aging. There is a preponderance of the leaf stems at the top portion and the intermediary portion of the trunk, large leaves extending umbrella-like over other leaves extending on the intermediary portion and lower portion of the trunk, the tip of the large leaves hanging on towards the lower portion of the trunk. The leaves have a leathery semi-gloss appearance on the top side and a leathery matte appearance on their underside. The variegation of the leaves appears from the underside as being transmitted through a translucent sheet.

My new variety of variegated Schefflera plant has shown consistent stability of variegation through three generations of propagation by airlayering. Older leaves do not fade or bleach with age. The light coloration, on the contrary, turns from chartreuse-cream to cream-mimosa.

A comparison between my new variety of variegated Schefflera plant and the variegated Schefflera plant disclosed in the Mastaler plant Pat. No. 4,187 reveals substantial differences. For example the Mastaler variegated Schefflera plant is characterized by an almost rosy coloration in the overall appearance of the plant with stems which are quite pink, while my new variety of variegated Schefflera plant is characterized by mimosa coloration in overall appearance with some mottling of green and with variegated stems of cream-mimosa and green. While the Mastaler plant has apparently a wide color range foliage from yellows to greens of various shades, my plant has a relatively narrow color range with abrupt contrasting change in coloration from cream-mimosa to two shades of green. While the Mastaler plant has a marble-like appearance extending over a large area of the leaves, on both sides of the rib, my plant has, on many leaves, a clear delineation between contrasting colors running, at least part of the length of the leaf, along the rib. The petioles of the Mastaler plant are uncharacteristically upwardly elongated while my new variety of Schefflera plant has petioles which are more horizontally elongated. The Mastler plant has an upright form, while my new variety of Schefflera plant, although also upright, has an umbrella-like appearance at its top due to each compound leaf itself having an umbrella-like appearance.

The following is a detailed description of my new variety of variegated Schefflera plant, with Exotica Horticultural Color Guide as the reference source for color determination, based on observations made of specimens grown in my nursery in Venice, Fla.

Parentage: Seedling of *Brassaia actinophylla.*
Propagation: Airlayering.
Plant:
*Form.*—Upright — compact.
*Growth.*—Very vigorous.
*Blooming habits.*—Has not bloomed yet.
Height: 10 to 15 feet (3 to 4.5 meters).
Spread: 4 to 6 feet (1.2 to 1.8 meters).
Foliage: Leaflets: 8 to 12 per rack.
Size: 8 to 12 inches (18 to 30 cm), and more, in length $2\frac{1}{2}$ to $3\frac{1}{2}$ inches (6.4 to 12 cm) in width.
Shape: Oblanceolate.
Foliage color:

*Top side.*—Variegated chartreuse No. 78 (new growth) — or cream No. 1-mimosa No. 2 (old growth), pine green No. 68 and moss green No. 82.
*Underside.*—Variegated.
Texture:
*Top side.*—Leathery semi-gloss.
*Underside.*—Leathery flat.
Ribs and veins: Ordinary.
Edge: Smooth.
Serration: None.
Leaf stem:
*Color.*—Variegated like the leaf — cream-mimosa and pine green.
Wood:
*New growth.*—Variegated.
*Old growth.*—Changing to gray at base of trunk.
Bark: Smooth.
Proposed denomination: Schefflera Reschii.

I claim:

1. A new and distinct variety of Schefflera plant of the species *Brassaia actinophylla* substantially as herein shown and described, characterized particularly as to novelty by the overall variegation of leaves, stems, and trunk from mimosa to green, close noded position of stems and upright rapid growth with leaves of leathery semi-gloss appearance on the top side and leathery matte appearance on the underside, and with a preponderance of leaf stems at the top portion and the intermediary portion of the plant extending umbrella-like with leaves hanging on towards the lower portion of the plant.

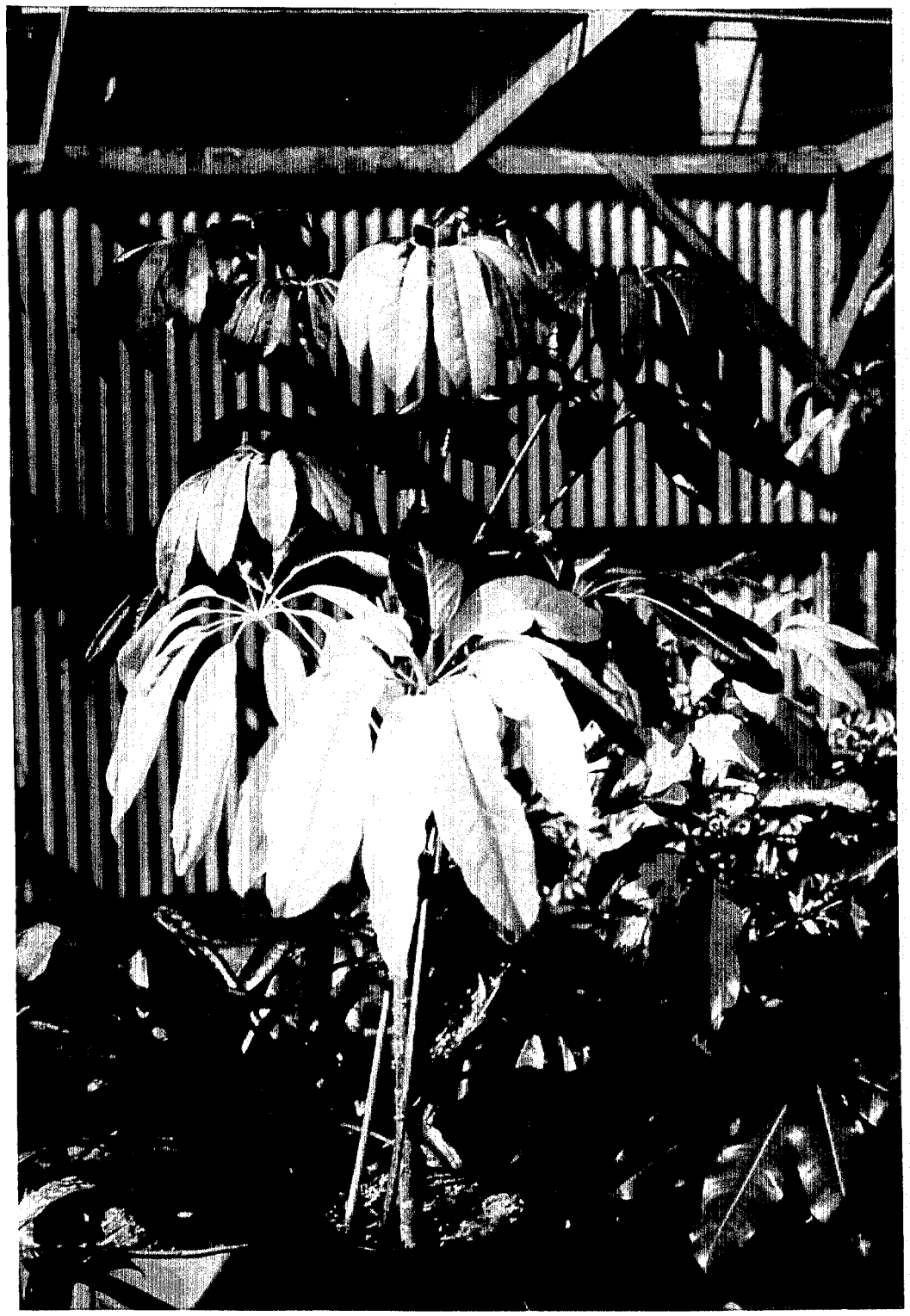

* * * * *